United States Patent [19]

Ouchi et al.

[11] Patent Number: 4,495,134
[45] Date of Patent: Jan. 22, 1985

[54] METHOD FOR MANUFACTURING A FLEXIBLE TUBE FOR AN ENDOSCOPE

[75] Inventors: Teruo Ouchi, Kawagoe; Hiromichi Shibuya, Tokyo, both of Japan

[73] Assignee: Kabushiki Kaisha Medos Kenkyusho, Japan

[21] Appl. No.: 441,998

[22] Filed: Nov. 16, 1982

[30] Foreign Application Priority Data

Nov. 17, 1981 [JP] Japan ................................. 56-184060

[51] Int. Cl.³ ...................... B29C 17/07; B29C 19/00; B29C 23/00; B29D 9/04
[52] U.S. Cl. .................................... 264/516; 264/512; 264/248; 264/254; 264/573; 264/273
[58] Field of Search ............... 264/512, 514, 515, 516, 264/573, 230, 248, 254, 273

[56] References Cited

U.S. PATENT DOCUMENTS

| 2,027,962 | 1/1936 | Currie | 264/230 |
| 3,276,941 | 10/1966 | Burns | 264/248 |
| 3,560,295 | 2/1971 | Kimbrell et al. | 264/516 |

FOREIGN PATENT DOCUMENTS 7106372 11/1971 Netherlands ......................... 264/516

Primary Examiner—Jan Silbaugh
Assistant Examiner—Hubert C. Lorin
Attorney, Agent, or Firm—Steinberg & Raskin

[57] ABSTRACT

A flexible tube for use in an endoscope comprises a flexible basic tubular core structure and a homogeneous thermoplastic synthetic resin tube bonded to the outer surface of the tubular core structure to form a coating layer by positioning the synthetic resin tube tightly over the basic tubular core structure with a contact pressure therebetween and heating the synthetic resin tube to a temperature higher than a softening point of the thermoplastic synthetic resin forming the same. A flexible tube having flexibility which varies in a step-wise manner from one end of the tube to the other is obtained by integrally bonding as a whole two or more homogeneous thermoplastic synthetic resin tube sections formed of respective resin materials having different hardnesses to the outer surface of the tubular core structure to form a coating layer in an analogous manner. The ends of adjacent tube sections substantially abut each other and upon heating the tube sections to a temperature higher than a softening point of any one of them, the regions of the respective pairs of abutting tube section ends are heated to a temperature substantially near a melting point of the tube section having the higher melting point to successively fuse the respective pairs of abutting tube section ends together.

8 Claims, 5 Drawing Figures

METHOD FOR MANUFACTURING A FLEXIBLE TUBE FOR AN ENDOSCOPE

BACKGROUND OF THE INVENTION

The present invention relates generally to flexible tubes for endoscopes and, more particularly, to a new and improved flexible tube for endoscopes and a method for manufacturing the same characterized by the arrangement and manner of formation of a coating of the flexible tube.

Generally, conventional flexible tubes for endoscopes are formed of a basic tubular core structure consisting of a metallic tubular spiral, sometimes referred to as FLEX, whose outer surface is covered by a meshwork tube, the outer surface of the tubular core structure itself being covered in one of two ways. In a first construction, a previously molded synthetic resin tube has covered the basic tubular core structure while in a second typical construction, a thermoplastic elastic body is directly molded around the tubular core structure so as to cover the same.

In the flexible tube of the first type described above, the basic tubular core structure is not adhered to the premolded synthetic resin tube and, consequently, wrinkles are often formed in the outer surface of the flexible tube as the latter is guided around a curved path during the introduction of the flexible tube into the body cavity. Another problem is that the flexible tube is not sufficiently rigid in compression so as to resist the compressive forces on the tube caused during the introduction thereof into the body cavity. Moreover, the well known flexible tubes of this type have also lacked good torsional rigidity, i.e., have poor rotation following characteristics, so that twists are often caused to be formed in the flexible tube by ordinary rotary manipulation thereof and such twists once formed frequently cause the flexible tube to become caught between inner walls or folds of the body cavity. Thus, introduction of such conventional flexible tubes is often painful to the patient and it is not always possible achieve a smooth introduction in any event. Furthermore, twists formed in the flexible tube can prevent the physician operating the endoscope from observing a desired region or object at a certain location through the forward end of the flexible tube.

In the conventional flexible tube construction of the latter type described above, some of the thermoplastic elastic material often protrudes through gaps present in the basic tubular core structure so as to extend into the inner surface of the flexible tube thereby causing an unevenness therein, such protrusion of the thermoplastic elastic material occurring in an uneven manner. As a result, it has frequently not been possible to obtain a uniform coating wall thickness relative to the central axis of the flexible tube. This fact has made it difficult to obtain a homogeneous flexible tube and adversely affects the flexibility of the tube which, of course, must be uniform when the flexible tube is bent during its introduction. In order to alleviate this problem, an arrangement is disclosed in Japanese patent publication No. 1980-17577 in which the basic tubular core structure is first coated with latex through immersion, drying, and solidification steps and the like, whereupon the latex covered core structure is then coated with thermoplastic material which is, in turn, molded thereon. Although this arrangement avoids the protrusion of the thermoplastic material into the basic tubular core structure, it has often resulted in complicated manufacturing processes while requiring large-sized molding machines. Accordingly, this arrangement has not been widely adopted.

SUMMARY OF THE INVENTION

Accordingly, it is an object of the present invention to provide new and improved flexible tubes for endoscopes and methods of manufacturing the same which overcome the disadvantages of conventional flexible tubes as described above.

It is a particular object of the present invention to provide a new and improved flexible tube for an endoscope and a method for manufacturing the same wherein the formation of wrinkles during introduction thereof is avoided and which provides uniformity of flexibility and improved torsional rigidity or rotation following characteristics so as to reduce the formation of twists in the flexible tube.

Another object of the present invention is to provide a new and improved method of manufacturing a flexible tube for an endoscope having a simplicity not found in the prior art.

Still another object of the present invention is to provide a new and improved flexible tube for an endoscope having improved maneuverability characteristics.

Briefly, in accordance with the present invention, these and other objects are obtained by providing a flexible tube for use in an endoscope comprising a flexible basic tubular core structure and a homogeneous thermoplastic synthetic resin tube bonded to the outer surface of the tubular core structure to form a coating layer by positioning the synthetic resin tube tightly over the basic tubular core structure with a contact pressure therebetween and heating the synthetic resin tube to a temperature higher than a softening point of the thermoplastic synthetic resin forming the same. A flexible tube having flexibility which varies in a step-wise manner from one end of the tube to the other is obtained by integrally bonding as a whole two or more homogeneous thermoplastic synthetic resin tube sections formed of respective resin materials having different hardnesses to the outer surface of the tubular core structure to form a coating layer in an analogous manner. The ends of adjacent tube sections substantially abut each other and upon heating the tube sections to a temperature higher than a softening point of any one of them, the regions of the respective pairs of abutting tube section ends are heated to a temperature substantially near a melting point of the tube section having the higher melting point to successively fuse the respective pairs of abutting tube section ends together.

DESCRIPTION OF THE DRAWINGS

A more complete appreciation of the present invention and many of the attendant advantages thereof will be readily understood by reference to the following detailed description when considered in connection with the following non-limiting drawings wherein.

DESCRIPTION OF THE PREFERRED EMBODIMENTS

Figure 1:
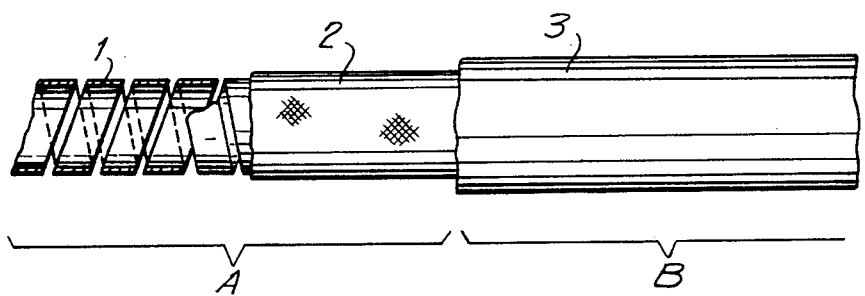
FIG. 1 is a side elevation view, partly in section and partly broken away, of a first embodiment of a flexible tube in accordance with the present invention.
Figure 2:
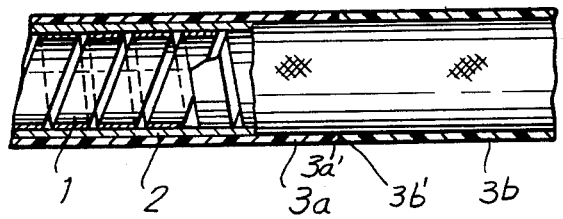
FIG. 2 is a view similar to FIG. 1 illustrating a second embodiment of a flexible tube in accordance with the present invention.

Referring now the drawings wherein like reference characters designate identical or corresponding parts throughout the several views, and more particularly to FIGS. 1 and 2 thereof, preferred embodiments of a flexible tube in accordance with the present invention are illustrated. Each embodiment comprises a metallic tubular spiral 1 which is resistant to collapsing under external pressure and which is adapted to accommodate and provide protection for various elements and components generally found in endoscopes such, for example, as the optical fiber bundle and a channel receiving means for manipulating forceps and the like. The metallic tubular spiral 1 is provided with a suitable flexibility for its intended use. The metallic tubular spiral 1 is tightly covered around its outer surface with a meshwork tube 2 which functions to restrict longitudinal stretching of the metallic tubular spiral 1. The metallic tubular spiral 1 and meshwork tube 2 constitutes a basic tubular core structure, designated A in FIG. 1, and is substantially similar to prior art core structures of this type.

In accordance with the present invention, the basic tubular core structure A is tightly covered around its outer surface with a thermoplastic synthetic resin tube 3. The tube 3 may be formed of material such as polyurethane, soft vinyl chloride, polyethylene or the like. The invention is characterized by the manner in which the outer surface of the basic tubular core structure A is tightly covered by the tube 3 and the flexible tube resulting therefrom. More particularly, the thermoplastic synthetic resin tube 3 is homogeneously prepared prior to incorporation in the flexible tube. The synthetic resin tube 3 is positioned tightly over the basic tubular core structure A with a contact pressure therebetween by following a procedure wherein a mandrel having an outer diameter substantially corresponding to an inner diameter of the metallic tubular spiral 1 is inserted into the interior of the metallic tubular spiral 1 so as to temporarily close the hollow interior of the basic core structure, positioning a forcibly enlarged open end of the homogeneous thermoplastic synthetic resin tube 3 over one end of the basic tubular core structure A and supplying or injecting compressed air or other suitable gas into the interior of the thermoplastic synthetic resin tube 3 through its other end. In this manner, the thermoplastic synthetic resin tube 3 is inflated until its inner diameter is sufficiently enlarged to permit the thermoplastic synthetic resin tube 3 to be fed over the meshwork tube 2 of the tubular core structure A.

In a case where the thermoplastic synthetic resin tube 3 has a sufficient flexibility so that its inner diameter can be greatly enlarged under the effect of the injection of compressed air into it, another procedure for tightly positioning the thermoplastic synthetic resin tube 3 over the basic tubular core structure A with a contact pressure therebetween can be employed. In this procedure, the interior of the flexible basic tubular core structure is temporarily closed, such as in the manner described above, whereupon an open end of the thermoplastic synthetic resin tube 3 is releaseably fixed on one end of the basic tubular core structure A, such as by tying or otherwise securing the same thereto. The tube 3 is then inflated by injecting or supplying compressed air into the interior thereof. The thermoplastic synthetic resin tube is then progressively rolled back over and around the basic tubular core structure A from the secured end towards the opposite end thereof so that the outer surface of the meshwork tube 2 is covered around its outer side with the tube 3. Thus, the thermoplastic synthetic resin tube 3 is progressively rolled back from the fixed end thereof to develop the synthetic resin tube axially along the basic tubular core structure such that the originally outer surface of the synthetic resin tube is positioned over the outer surface of the basic tubular core structure A.

With the synthetic resin tube 3 positioned over the tubular core structure A by a method described above or the like, the injection of compressed air may be terminated or an amount of compressed air already injected into the tube 3 is exhausted or vented, to position the thermoplastic synthetic resin tube 3 tightly over the basic tubular core structure A on the meshwork tube 2 with a contact pressure therebetween resulting from the inherent contractive forces which tend to restore the synthetic resin tube to its unstretched condition.

The thermoplastic synthetic resin tube 3 tightly positioned over the basic tubular core structure A is then thermally treated by heating the same to a temperature higher than the softening point of the synthetic resin forming the tube 3. The tube 3 is thus softened or becomes molten, depending upon the temperature at which the tube 3 is treated and the material thereof drawn to protrude into the tissue or fabric mesh of the meshwork tube 2 and becomes integrally fixed thereto upon plasticizing. In this manner, the thermoplastic synthetic resin tube 3 forms a coating layer which is integrally bonded to the outer surface of the basic tubular core structure A.

The forces of adhesion by which the softened thermoplastic synthetic resin tube 3 is bound to the meshwork tube 2 is sufficient to prevent wrinkles from being formed due to compressive forces which occur during introduction of the flexible tube and, moreover, prevents twists from being formed in the flexible tube during rotational manipulation thereof. The flexible tube can be provided if desired with further treatment or working in connection with its finishing. In order to further enhance the adhesion forces binding the thermoplastic synthetic resin tube 3 to the tubular core structure A, the tube 3 is preferably heated close to its melting point so that the molten resin will be partially fused into the fabric or tissue meshes of the meshwork tube 2. In this manner, a bonding force between the tube 3 and the meshwork tube 2 is substantially improved.

During the thermal treatment steps described above, an external pressure can be applied to the thermoplastic synthetic resin tube 3 by means of a die or the like while the tube 3 is in its softened or semi-molten state by virtue of the thermal treatment at a temperature higher than the softening point thereof in order to still further improve the bonding of the tube 3 around the meshwork tube 2. A portion of the flexible tube completed in accordance with the arrangement described above is designated B in FIG. 1.

Referring now to FIG. 2, another embodiment of the flexible tube in accordance with the present invention is illustrated in which the parts designated by the same reference numerals as in FIG. 1 are similar to those of the embodiment illustrated therein designated by those reference numerals. In the embodiment of FIG. 2, the basic tubular core structure A consists of the metallic tubular spiral 1 and the meshwork tube 2 which externally covers the spiral 1. The outer surface of the meshwork tube 2 is tightly covered with a thermoplastic synthetic resin tube 3 comprising at least two homogeneous thermoplastic synthetic resin tube sections respectively formed of resin material having different hardnesses. The synthetic resin tube sections are integrally bonded as a whole to the outer surface of the tubular core structure over the substantial length thereof to form a coating layer in a manner described below.

A flexible tube for an endoscope may have various constructions depending upon its particular intended use. For example, when it is desired to introduce the front end of a flexible tube which is adapted for permitting observation deep within a particular digestive organ, such as in the case of the diagnosis and/or treatment of the duodenum, the tube must be introduced along a curved path defined by the organ from the mouth. To achieve such introduction in a smooth manner, it is well known that the portion of the tube adjacent to the manipulator unit of the endoscope should have a relatively high rigidity or relatively low flexibility while the portion of the tube adjacent to its front end which is adapted for observation should have a relatively high flexibility, in order to avoid difficulty in the feeding or introduction of the flexible tube in a smooth manner along the curved path of the organ. Thus, if the front end of the endoscope flexible tube which has been adapted to provide a means for observing the organ cannot be smoothly guided along the curve presented by the organ wall within the body cavity during introduction of the flexible tube, the front end may damage the organ wall or, in an extreme case, even rupture the organ wall. Not only are solutions to the problems of injury or rupture to the organ desired but, additionally, an arrangement whereby the flexible tube is prevented from becoming caught on the organ wall and thereby causing the patient pain is also sought.

In view of the practical manners in which an endoscope is used, such as described above, in the embodiment illustrated in FIG. 2, the flexible tube is provided with a flexibility which varies in a step-wise manner over its length. Referring to FIG. 2, at least two thermoplastic synthetic resin tubes $3a$, $3b$ are provided which are respectively formed of resin material having different hardnesses. The thermoplastic synthetic resin tube sections are successively tightly positioned over the basic tubular core structure with a contact pressure therebetween and have ends $3a'$ and $3b'$ which abut each other. The respective abutting ends $3a'$ and $3b'$ of adjacent tube sections $3a$ and $3b$ are adapted so as to be mutually fusible together in a compatible manner. Furthermore, the respective thermoplastic synthetic resin tube sections $3a$ and $3b$ are formed of materials which preferably have their melting points as close to each other as possible.

The thermoplastic synthetic resin tube sections $3a$ and $3b$ may be tightly positioned on the outer surface of the meshwork tube 2 by any one or a suitable combination of the two methods described above without any practical difficulty. The thermoplastic synthetic resin tube section $3a$ and $3b$ thus positioned on the outer surface of the meshwork tube 2 are heated to a temperature higher than the softening point of the tube section having the highest softening point and, preferably, substantially near the melting point of the tube section whose melting point is higher than that of the other tube sections, so that the softened or molten thermoplastic synthetic resin material partially flows into the fabric or tissue mesh of the meshwork tube 2 so that after cooling, the thermoplastic synthetic resin tube sections are integrally bonded to the outer surface of the tubular core structure. Moreover, during the heat treatment described above, at least the regions of the respective pairs of abutting tube section ends $3a'$ and $3b'$ are heated to a temperature substantially near the melting point of the tube section having the higher melting point to fuse the respective pairs of abutting tube section ends together. In this manner, the thermoplastic synthetic resin tube sections are integrally bonded as a whole to the outer surface of the tubular core structure. This provides a smooth coating over the tubular core structure without the presence of any junctures, seams or the like.

Although the embodiment of FIG. 2 has been described in connection with two thermoplastic synthetic resin tube sections $3a$ and $3b$, it will be understood from the foregoing that more than two thermoplastic synthetic resin tube sections of respective different hardnesses may be successively fused together, end to end, so that the resulting flexible tube will have a flexibility which varies in a step-wise fashion over its length. The flexibility increases progressively from the portion of the flexible tube adjacent to the manipulator unit of the endoscope towards the front end thereof which is adapted to provide observation.

Figure 3:
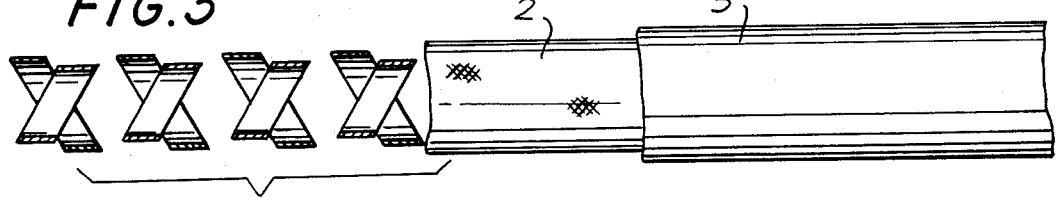
FIG. 3 is a view similar to FIG. 1 illustrating a modification of the embodiment illustrated therein.
Figure 4:
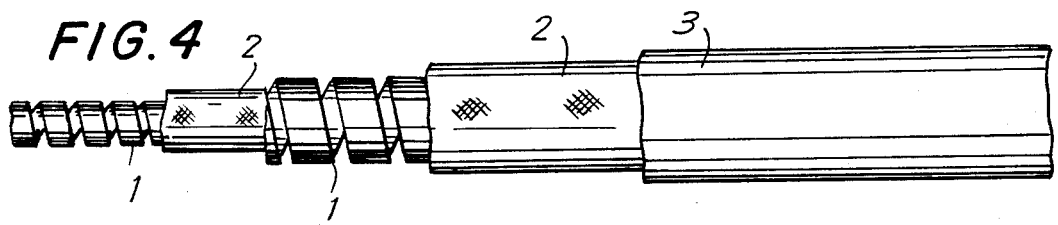
FIG. 4 is a view similar to FIG. 1 illustrating a second modification of the embodiment illustrated therein.

Although the present invention has been described for the sake of simplicity of description with respect to a basic tubular core structure A comprising a single metallic tubular spiral which is covered with a single meshwork tube, it should be understood that the present invention is not limited to such a construction of the basic tubular core structure but may also be applied, without restriction, for example to basic tubular core structures comprising a combination of clockwise and counter-clockwise tubular spirals as seen in FIG. 3 or to basic tubular core structures comprising metallic tubular spirals and meshwork tubes positioned alternately one over the other in a multi-layered manner as seen in FIG. 4.

Figure 5:
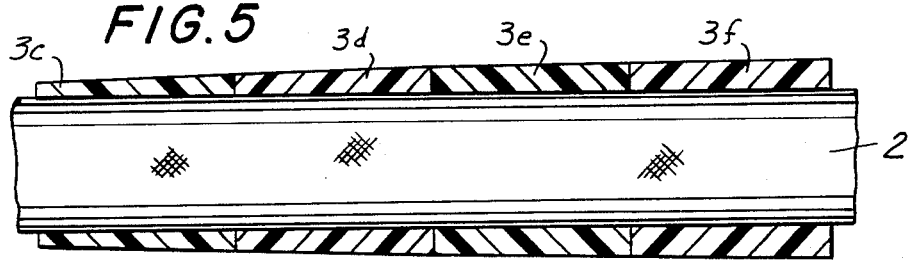
FIG. 5 is a view similar to FIG. 2 and illustrating a modification of the embodiment illustrated therein.

With respect to the embodiment illustrated in FIG. 2, although the flexible tube shown therein incorporates a basic tubular core structure covered by a plurality of thermoplastic synthetic resin tube sections having uniform inner diameters and wall thicknesses, it is understood that the embodiment can be modified as illustrated in FIG. 5 by covering the tubular core structure with a plurality of thermoplastic synthetic resin tube sections $3c$, $3d$, $3e$ and $3f$, each tube section having a uniform inner diameter and a wall thickness which varies from the thinnest at one end to the thickest at the other end. The plurality of thermoplastic tube sections successively abut one another, end to end, in a manner such that no offset or discontinuity if formed at any juncture or seam. The respective pairs of abutting ends of adjacent tube sections are then fused together by heating and melting the tube material so as to obtain a continuous seamless outer surface of the flexible tube.

It will be understood from the foregoing description that in accordance with the present invention the flexible tube comprising the basic tubular core structure externally covered with the thermoplastic synthetic resin tube is heated to a temperature higher than the softening point of the synthetic resin tube to thereby tightly bond the synthetic resin tube to the basic tubular core structure. This construction permits the synthetic resin tube which constitutes a covering for the basic tubular core structure to follow the bending and rotation of the flexible tube without forming wrinkles and twists, respectively. This construction also permits the portions of the flexible tube adjacent to the manipulator unit and to the front end of the flexible tube which is adapted for observation to be maintained in the same orientation so that the flexible tube is sufficiently resistant to compressive forces arising during the introduction of the flexible tube into the body cavity thereby remarkably improving the maneuverability of the flexible tube. Furthermore, problems such as the flexible tube catching on the organ wall within the body cavity are avoided by a flexible tube constructed in accordance with the present invention thereby minimizing any pain caused to the patient. The outer surface of the flexible tube is also heated in molding and integration resulting in this outer surface being quite smooth. The outer surface of the basic tubular core structure is covered with the homogeneous thermoplastic synthetic resin tube which has been premolded so that the flexible tube obtains a uniform outer coating of the synthetic resin which is integrally bonded around the basic tubular core structure by heat treatment without the protrusion of thermoplastic synthetic resin material into the basic tubular core structure. Thus, a flexible tube for an endoscope which is substantially uniform in all respects is provided by the present invention. Only one step of the manufacturing process may be to thermally mold the basic tubular core structure externally covered by the thermoplastic synthetic resin tube and the equipment necessary force the manufacturing of the flexible tube in accordance with the invention is therefore simplified so that the product can be manufactured at a relatively low cost.

A step-wise or progressive variation of hardness in the flexible tube over its length has conventionally been achieved, for example, by mechanically connecting a plurality of plastic tube pieces of different hardness to the basic core structure. Such mechanical connection inevitably results in discontinuities or offsets and rigid portions at the junctures or seams formed thereby, thereby causing the flexible tube to catch on the inner wall of the body cavity during introduction of the flexible tube preventing a smooth introduction of the tube into the body cavity. In accordance with the present invention, on the contrary, a plurality of thermoplastic synthetic resin tube pieces of respective different hardnesses are successively fused together and integrally bonded to the tubular core structure and, consequently, a flexible tube having a smooth outer surface is provided which can be flexed in conformity with a curved path presented by the organ within the body cavity.

Obviously, numerous modifications and variations of the present invention are possible in the light of the above teachings. It is therefore to be understood that within the scope of the claims appended hereto the invention may be practiced otherwise than as specifically disclosed herein.

What is claimed is:

1. In a method for manufacturing a flexible tube for use in an endoscope, the flexible tube comprising a basic tubular core structure including at least an inner metallic tubular spiral having an outer side and an outer meshwork tube covering the outer side of the metallic tubular spiral, the improvement comprising the steps of:

(a) locating a preformed homogeneous thermoplastic synthetic resin tube over the outer surface of the meshwork tube with a contact pressure therebetween to form an intermediate product by the steps of temporarily closing the hollow interior of the basic tubular core structure;

positioning a forcibly enlarged open end of the homogeneous thermoplastic synthetic resin tube over one end of the basic tubular core structure;

inflating the thermoplastic synthetic resin tube by supplying compressed gas into the interior thereof until the inner diameter of the inflated termoplastic synthetic resin tube corresponds to the outer diameter of the basic tubular core structure;

feeding the thermoplastic synthetic resin tube axially over the basic tubular core structure;

reducing the internal overpressure in the interior of the thermoplastic synthetic resin tube after a desired length of said thermoplastic synthetic resin tube has been fed over the basic tubular core structure whereupon a contact pressure exists between the thermoplastic synthetic resin tube and the tubular core structure resulting from the inherent contractive forces tending to restore the synthetic resin tube to its unstressed condition; and (b) treating the intermediate product so that the thermoplastic synthetic resin of the thermoplastic synthetic resin tube partially flows into the mesh of the meshwork tube by the step of heating the thermoplastic synthetic resin tube to a temperature higher than a softening point of the thermoplastic synthetic resin forming the same, whereupon the thermoplastic synthetic resin protrudes into the mesh of the meshwork tube and so that upon plasticizing the resin tube forms a coating layer bonded integrally to the basic tubular core structure.

2. A method according to claim 1 wherein the basic tubular core structure comprises a multi-layered structure including a clockwise extending metallic tubular spiral and a counterclockwise extending metallic tubular spiral.

3. A method according to claim 1 wherein the basic tubular core structure comprises a multi-layered construction of metallic tubular spirals and meshwork tubes alternately covering one another.

4. In a method for manufacturing a flexible tube for use in an endoscope, the flexible tube comprising a basic tubular core structure including at least an inner metallic tubular spiral having an outer side and an outer meshwork tube covering the outer side of the metallic tubular spiral, the improvement comprising the steps of:

(a) locating a preformed homogeneous thermoplastic synthetic resin tube over the outer surface of the meshwork tube with a contact pressure therebetween to form an intermediate product by the steps of temporarily closing the hollow interior of the tubular core structure;

releasably fixing an open end of a homogeneous thermoplastic synthetic resin tube on one end of the basic tubular core structure;

inflating the thermoplastic synthetic resin tube by supplying compressed gas into the interior thereof;

rolling back the thermoplastic synthetic resin tube progressively from the releasably fixed end thereof to develop the synthetic resin tube axially along the basic tubular core structure so that the originally outer surface of the synthetic resin tube is positioned over the outer surface of the basic tubular core structure;

reducing the internal overpressure in the interior of the thermoplastic synthetic resin tube after completing said development of the synthetic resin tube along the basic tubular core structure to thereby tightly position the synthetic resin tube over the outer surface of the basic tubular core structure with a contact pressure therebetween; and (b) treating the intermediate product so that the thermoplastic synthetic resin of the resin tube partially flows into the mesh of the meshwork tube by the step of heating the thermoplastic synthetic resin tube to a temperature higher than a softening point of the thermoplastic synthetic resin forming the same, whereupon the thermoplastic synthetic resin protrudes into the mesh of the meshwork tube and so that upon plasticizing the resin tube forms a coating layer bonded integrally to the outer surface of the basic tubular core structure.

5. A method according to claim 4 wherein the basic tubular core structure comprises a multi-layered structure including a clockwise extending metallic tubular spiral and a counter-clockwise extending metallic tubular spiral.

6. A method according to claim 4 wherein the basic tubular core structure comprises a multi-layered construction of metallic tubular spirals and meshwork tubes alternately covering one another.

7. A method for manufacturing a flexible tube for use in an endoscope, the flexible tube having a flexibility which varies over its length comprising a basic tubular core structure including at least an inner metallic tubular spiral having an outer side and an outer meshwork tube covering the outer side of the metallic tubular spiral, comprising the steps of:

successively positioning at least two synthetic resin tube sections formed of resin material having mutually different flexibility tightly over a basic tubular core structure with a contact pressure therebetween and with adjacent tube sections substantially abutting at respective ends to form an intermediate product;

treating the intermediate product so that the thermoplastic resins of the tube sections partially flow into the mesh of the meshwork tube by heating said tube sections to a temperature higher than a softening point of any one of said thermoplastic synthetic resin tube sections; and heating the intermediate product at least in the regions of respective pairs of abutting tube section ends to a temperature substantially near a melting point of the tube section having the higher melting point to successively fuse the respective pairs of abutting tube section ends together, whereby the flexible tube has a flexibility which varies from one end thereof to the other.

8. A method as recited in claim 7 wherein each of said thermoplastic synthetic resin tube sections has a uniform inner diameter and a wall thickness which is thicker at one end of said tube section than at the other end thereof so that the outer diameter of said tube sections is greater at said one end of said tube section than at said other end thereof, and wherein adjacent tube sections abut at respective ends having substantially the same outer diameter.

* * * * *